United States Patent
Xu et al.

(10) Patent No.: US 8,927,897 B2
(45) Date of Patent: Jan. 6, 2015

(54) LASER MAINTENANCE TOOL

(75) Inventors: Raymond Ruiwen Xu, Carmel, IN (US); Timothy Paul Fuesting, Thorntown, IN (US); William J. Brindley, Indianapolis, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 1056 days.

(21) Appl. No.: 12/948,318

(22) Filed: Nov. 17, 2010

(65) Prior Publication Data

US 2012/0121382 A1 May 17, 2012

(51) Int. Cl.
*B23K 26/36* (2014.01)
*F01D 25/00* (2006.01)
*B23K 26/06* (2014.01)
*G01N 21/954* (2006.01)

(52) U.S. Cl.
CPC ............ *F01D 25/002* (2013.01); *B23K 26/365* (2013.01); *B23K 26/0635* (2013.01); *F05D 2230/72* (2013.01); *F05D 2230/80* (2013.01); *F05D 2260/80* (2013.01); *G01N 21/954* (2013.01)
USPC ............ 219/121.61; 219/121.68; 219/121.69; 219/121.83

(58) Field of Classification Search
CPC ............ G02B 23/2476; B23K 26/032; B23K 26/365; B23K 26/381; B23K 26/0635
USPC ............. 219/121.68, 121.69, 121.73, 121.83, 219/121.61, 121.62; 356/241.4
See application file for complete search history.

(56) References Cited

U.S. PATENT DOCUMENTS

| | | | |
|---|---|---|---|
| 4,982,065 A * | 1/1991 | Sandaiji et al. | 219/121.68 |
| 4,998,005 A | 3/1991 | Rathi et al. | |
| 5,164,565 A | 11/1992 | Addiego et al. | |
| 5,491,317 A | 2/1996 | Pirl | |
| 5,514,849 A | 5/1996 | Findlan et al. | |
| 5,653,897 A | 8/1997 | Findlan et al. | |
| 6,288,362 B1 * | 9/2001 | Thomas et al. | 219/121.84 |

(Continued)

FOREIGN PATENT DOCUMENTS

JP 8279657 10/1996
JP 2003-001465 A * 1/2003

OTHER PUBLICATIONS

Machine translation of Japan Patent Document No. 2003-001,465, May 2014.*

(Continued)

*Primary Examiner* — Geoffrey S Evans
(74) *Attorney, Agent, or Firm* — Barnes & Thornburg LLP

(57) ABSTRACT

In one form a maintenance device includes a flexible member with an inspection end sized to be inserted through an inspection port of a workpiece such as a gas turbine engine or a blade of a gas turbine engine. The maintenance device includes a directed energy member that in one form is configured to produce a double pulse laser with an interval time between a first one of the pulses and a second one of the pulses greater than the time of either the first one of the pulses or the second one of the pulses. The first one of the pulses is sufficiently powerful to produce a quantity of debris upon irradiation of the workpiece. The debris produced from the first one of the pulses can be evaporated by the second one of the pulses to eliminate and/or reduce a recast layer on the workpiece.

33 Claims, 7 Drawing Sheets

(56) References Cited

U.S. PATENT DOCUMENTS

| | | | |
|---|---|---|---|
| 6,542,230 B1* | 4/2003 | Luke | 356/241.1 |
| 6,593,540 B1 | 7/2003 | Baker et al. | |
| 6,664,498 B2* | 12/2003 | Forsman et al. | 219/121.6 |
| 6,710,280 B2 | 3/2004 | Mazumder et al. | |
| 6,774,338 B2 | 8/2004 | Baker et al. | |
| 6,992,263 B1 | 1/2006 | Baker et al. | |
| 7,012,216 B2 | 3/2006 | Baker et al. | |
| 7,030,337 B2 | 4/2006 | Baker et al. | |
| 7,038,162 B2 | 5/2006 | Baker et al. | |
| 7,112,761 B2 | 9/2006 | Hughes et al. | |
| 7,307,237 B2 | 12/2007 | Hughes et al. | |
| 2004/0169021 A1 | 9/2004 | Baker et al. | |
| 2005/0103755 A1 | 5/2005 | Baker et al. | |
| 2005/0218122 A1* | 10/2005 | Yamamoto et al. | 219/121.61 |
| 2005/0235493 A1 | 10/2005 | Philip et al. | |
| 2006/0000269 A1 | 1/2006 | Lemieux et al. | |
| 2006/0042083 A1* | 3/2006 | Baker et al. | 219/121.6 |
| 2006/0088984 A1* | 4/2006 | Li et al. | 219/121.69 |
| 2006/0091125 A1* | 5/2006 | Li et al. | 219/121.69 |
| 2006/0140230 A1* | 6/2006 | Sun et al. | 372/25 |
| 2006/0175307 A1 | 8/2006 | Hughes et al. | |
| 2006/0175308 A1 | 8/2006 | Hughes et al. | |
| 2006/0291998 A1* | 12/2006 | Dube et al. | 415/118 |
| 2007/0138150 A1 | 6/2007 | Gualtieri | |
| 2010/0171956 A1 | 7/2010 | Sappey et al. | |

OTHER PUBLICATIONS

International Search Report and Written Opinion, PCT/US2011/061134, Rolls-Royce Corporation, May 18, 2012.

* cited by examiner

LASER MAINTENANCE TOOL

TECHNICAL FIELD

The present invention generally relates to maintenance of devices using borescopes, and more particularly, but not exclusively, to borescope maintenance incorporating lasers.

BACKGROUND

Performing maintenance using borescopes remains an area of interest. Some existing systems have various shortcomings relative to certain applications. Accordingly, there remains a need for further contributions in this area of technology.

SUMMARY

One embodiment of the present invention is a unique repair apparatus and method. Other embodiments include apparatuses, systems, devices, hardware, methods, and combinations for repair of damaged gas turbine engine components. Further embodiments, forms, features, aspects, benefits, and advantages of the present application shall become apparent from the description and figures provided herewith.

DETAILED DESCRIPTION OF THE ILLUSTRATIVE EMBODIMENTS

Figure 1:
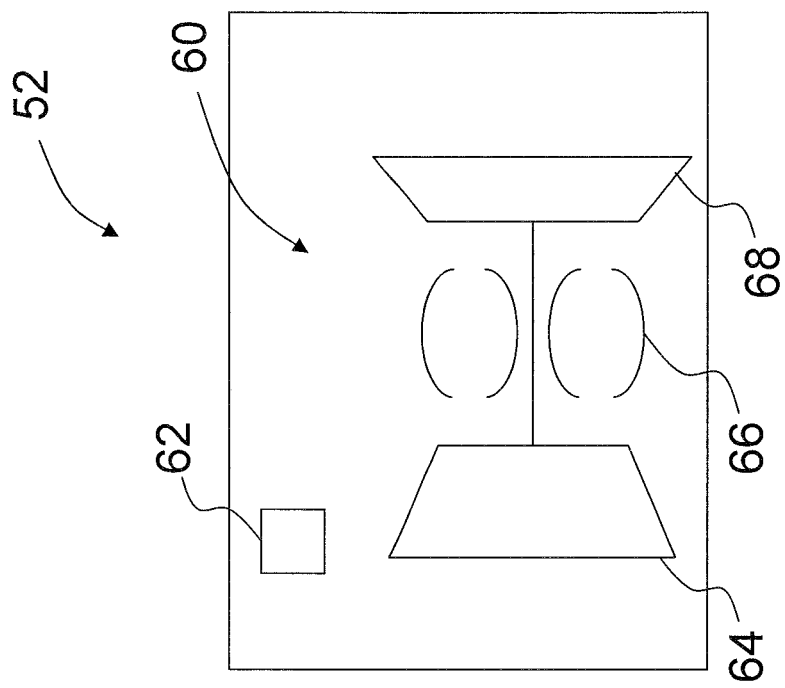
FIG. 1 depicts one embodiment of the present application.
Figure 1:
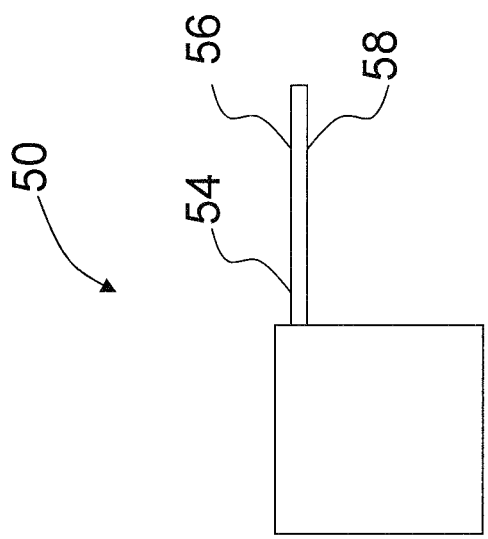

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With reference to FIG. 1, a maintenance device 50 is depicted in proximity to a workpiece 52. As will be described further below, the maintenance device 50 can be used by manufacturing or field personnel, among potential others, to service the workpiece 52. The maintenance device 50 includes a flexible member 54 having a borescope 56 and a directed energy member 58. The flexible member 54 permits the borescope 56 and directed energy member 58 to be delivered to areas of the workpiece 52 that are potentially inaccessible without a disassembly or teardown of the workpiece 52. For example, the flexible member 54 can be inserted into the workpiece 52 and manipulated around obstacles that otherwise block a line of sight of a portion of the workpiece 52. The flexible member 54 can be any suitable construction, material, and/or composition to permit flexible movements. In some forms the flexible member 54 can have an internal opening to permit passage of information or materials.

The borescope 56 can be used to provide images or other useful information of an area of interest in the workpiece 52, whether or not that area of interest is hidden from convenient view by one or more obstacles. Additionally and/or alternatively the borescope 56 can be coupled with or otherwise include useful devices for delivering material and/or manipulating objects of the workpiece 52 to the area of interest. The images or functions provided by the borescope 56 can occur near or proximate an end of the flexible member 54. In some applications the borescope 56, or portions thereof, can be located internal to the flexible member 54.

The directed energy member 58 is used to operate upon the workpiece 52 and can be coupled internal or external to the flexible member 54. In some applications the directed energy member 58 can be used to cut and/or heat the workpiece 52, join portions of the workpiece 52, or perform other construction processes such as repair and maintenance. Some additional non-limiting processes include welding, brazing, bonding, hole drilling, peening, metal build-up or metal addition, building-up, re-surfacing, surface cleaning, forming, heat treatment, and material removal. In the example of peening, it is possible to produce peened surfaces having no negative surface contour effects and a precise special distribution of residual stress. The energy delivered by the directed energy member 58 can be used for materials and processes requiring production of tailored microstructures, geometric features, surface finishes, and residual stresses.

The flexible member 54 can also be coupled with other devices such as those that enable gas, powder, and/or wire delivery. In some embodiments the maintenance device 50 can include motion, aiming, and locating controls for the borescope 56 and/or directed energy member 58. The maintenance device 50 can also include a material removal channel.

The maintenance device 50 can use the flexible member 54 in conjunction with the directed energy member 58 to perform a variety of tasks. In one non-limiting embodiment the maintenance device 50 can be used to remove material from the workpiece 52 using the directed energy member 58. The device 50 can also be used to build up a material upon the workpiece 52 using directed energy member 58 in conjunction with devices such as those that enable gas, powder, and/or wire delivery. Controls for moving, aiming, and locating the device 50, such as the borescope 56, can be used when removing material or adding material.

The directed energy member 58 can take the form of a laser which can be designed to laser objects in a variety of manners such as, but not limited to, continuous, pulse, or groupings of laser pulses. In one non-limiting form the groupings of pulses are formed as pairs. Each pulse in a pair of pulses can have a duration that may not be the same of the other pulse, although in some applications the pulses can have the same duration. Furthermore, the duration of either or both pulses in one pair can be the same or different than the duration of either or both pulses in another pair. In one embodiment the pulses can have a duration of about 3 nanoseconds (ns). The time interval between the pulses can be about 100 ns, but in some applications the time interval can be in a range of 30 ns to 150 ns. The time between pairs of pulses can be in a range of 100 microseconds (μs) to 100 milliseconds (ms). Similar to the pulse duration described above for individual pulses within a pair, the time interval between pulses and the time between pairs of pulses can vary with time as the laser develops successive pairings of pulses. In short, a great variety of duration, time interval, and time between pairs of pulses can be implemented with the directed energy member 58.

The embodiments of the laser can take a variety of forms and have a variety of characteristics. The laser can be one of Nd:YAG, CO2, disk, or fiber. In addition, in some non-limiting forms the peak power of each laser pulse, such as the peak power of a 3 ns pulse, could reach 750 kW with a total energy of 2.4 milliJoule (mJ) and an intensity of $4 \times 10^{10}$ Watts per square centimeter ($W/cm^2$). In some forms a laser fiber having approximately 1 millimeter (mm) diameter can deliver average output power up to 8 kilowatts (kW). In certain applications, Q-switched fiber lasers can offer up to 2 mJ energy per pulse with peak power of more than 50 kilowatts (kW). Furthermore, any given pulse of the laser can have a unique power, energy, and intensity. It is also possible to have a repeating pattern of power, energy, and intensity. In short, like the variations described above regarding duration, time interval, and time between pairs of pulses, the pulses can also have variation in their power, energy, and intensity.

The directed energy member 58 can be moved at a variety of rates to affect a cut, or other procedure, upon the workpiece 52. The rate at which the directed energy member 58 is moved can be dependent upon thickness and material composition, among other attributes and/or criteria. In some applications the directed energy member 58 can be moved in a range of 0.2 mm per minute to 1.0 mm per minute.

The relative timing and grouping of pulses can be used on a workpiece 52 to discourage the formation of at least one of a material recast, stress concentrators, a heat affected zone, microcracking, re-deposition, and re-solidification. In the groupings of pulses described above the first one of the pulses is capable of producing debris, and in some cases can additionally or alternatively produce fast moving plasma. The plasma can dissipate after application of the first one of the pulses but the other debris can remain over the area of interest during the delay period between the first one of the pulses and the second one of the pulses. The second one of the pulses can be used to dissipate the debris such as through, but not limited to, vaporization. In some forms the second pulse can be used to superheat the debris. In some applications the debris can be completely dissipated, while in other applications the debris may only be partly dissipated.

The application of the directed energy member 58 by the maintenance device 50 of the present application can be performed in the presence of a working fluid which, in one form, is air but other working fluids are also contemplated. In some applications the maintenance device 50 can receive the assistance of an air flush onto the area of interest which can encourage the reduction of debris.

In one embodiment the workpiece 52 is a gas turbine engine 60 that includes a gas turbine engine inspection opening 62. The opening 62 can be a purpose designed access hole or an opening created by removing a panel or door or any other such hole through which the flexible member 54 can pass. In one form the opening 62 is a borescope inspection port. The opening 62 can take on a variety of shapes not limited to square and circle, and in some forms can have a dimension such as a diameter in the range of 4 mm to 10 mm. The flexible member 54 can be inserted into the opening 62 and be directed to an area of the gas turbine engine 60 to be operated upon by the borescope 56, the directed energy member 58, or other device coupled to the flexible member 54 to facilitate processing as described above. The gas turbine engine 60 can include, among other features, a compressor 64, combustor 66, and turbine 68. In one non-limiting example, the directed energy member 58 can be applied to a blade of the compressor 64 to affect a repair from foreign object damage. In some embodiments the workpiece 52 can include an aircraft (not shown) having the gas turbine engine 60 wherein the maintenance device 50 can be positioned relative to either to affect a process such as one described above.

Figure 2:
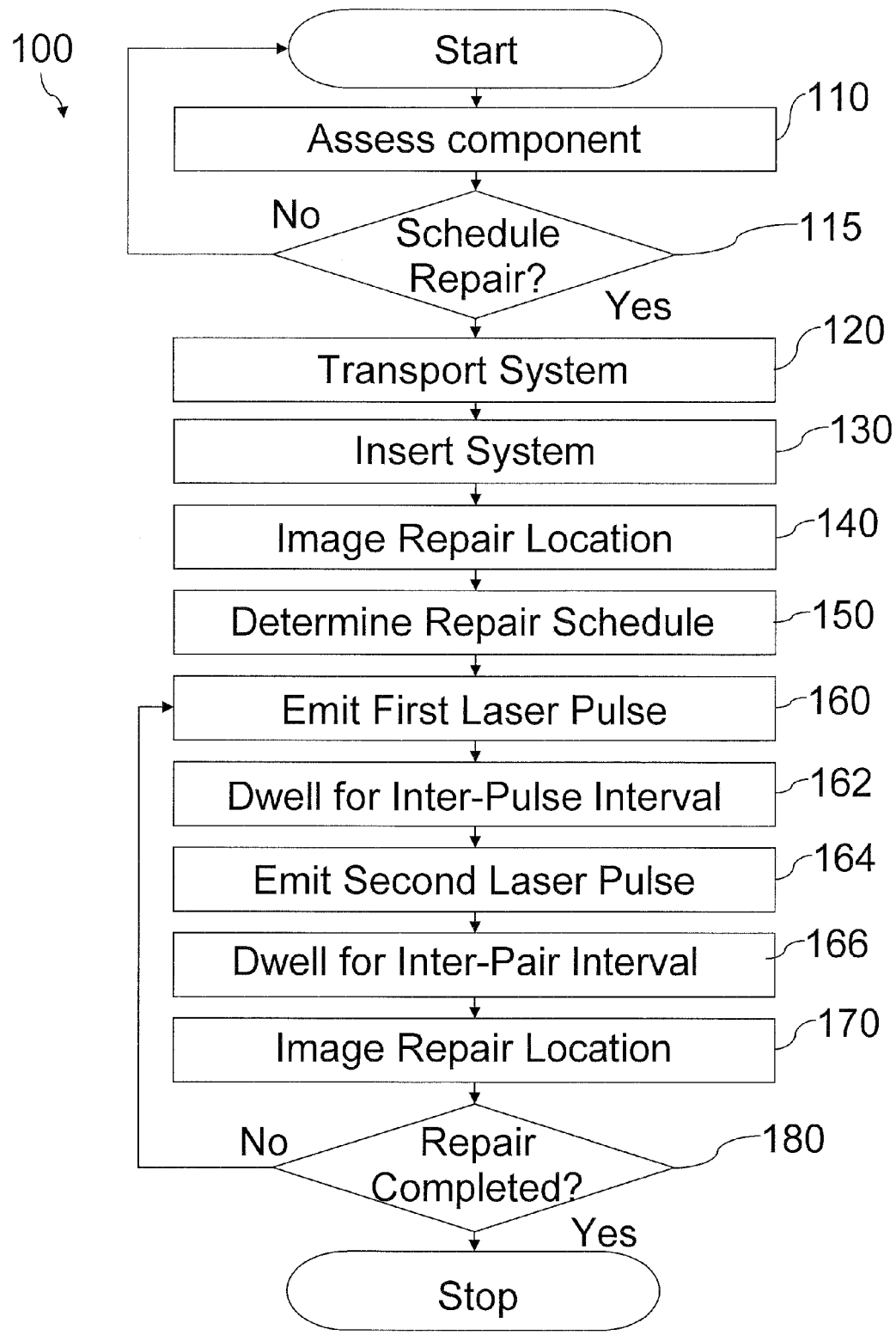
FIG. 2 is a flow chart of one embodiment of the present application.

Turning now to FIG. 2, one embodiment of the present application is illustrated in Procedure 100. The Procedure 100 is a non-limiting example of a method of operating the maintenance device 50. Not all operations are required in all embodiments of the present application, and in some cases alternative and/or additional operations can be included. Furthermore, some operations described below can be changed or altered as fits a particular application. Procedure 100 is initiated with an assessment in Operation 110. The assessment described in Procedure 110 can be for a component or a structure such as the gas turbine engine of an aircraft. The assessment can be a visual assessment where the component is viewed, a procedural assessment based on maintenance records or a component diagnostic system with signals indicating potential issues, to set forth just a few non-limiting examples.

Once an assessment is made in Operation 110, a decision is made whether a repair should be scheduled in Conditional 115. If a repair isn't scheduled, Procedure 100 returns to the start. With a positive response to Conditional 115, Procedure 100 continues with Operation 120 where one embodiment of the maintenance device 50 is transported to where it is required in the repair field. Such an embodiment could be a fully flexible fiber-hosted laser borescope system having any of the variations discussed above. The maintenance device 50 can be mobile to allow the directed energy member 58 to be operated in a repair field to allow repairs to components while the engine is still assembled to a structure of an aircraft.

After the maintenance device 50 is transported in Operation 120 and ready for set up, Operation 130 continues with inserting the flexible member 54 including the directed energy member 58, borescope 56, and any additional process device deemed necessary into an access hole in the workpiece 52 being repaired. Once the flexible member 54 has been inserted, the directed energy member can be flexed and bent around obstacles to reach a desired repair location. The borescope portion of the maintenance device 50 can aid in placement of the directed energy member 58.

An image of the repair location is taken in Operation 140. The image is then analyzed to determine a repair schedule in Operation 150. The repair schedule can include the selection of laser type, laser power, or laser speed to name just a few. The repair schedule can also determine the location and path of the laser and any other factors necessary to operate the desired repair.

Operation 160 starts the laser process by emitting the first laser pulse of a grouping of pulses at particular strength for a particular duration. Operation 162 follows Operation 160 with a dwell time between pulses, also referred to as an inter-pulse interval. The inter-pulse interval is followed by Operation 164 which emits the second laser pulse at a strength and duration for the second pulse. Operation 164 is followed by Operation 166 with a dwell time between groupings of pulses, also referred to as an inter-pair interval. During Operation 166, Operation 170 can be initiated to assess the progress of the repair. Conditional 180 decides whether the laser process should continue by repeating Operations 160 thru 170 or should stop thus signifying that the repair is complete.

To demonstrate the laser for potential repair applications such as in-situ, on-wing repairs of a gas turbine engine, laser cutting trials were performed on Ti and Ni alloy HPC blades. In one embodiment technical requirements for potential on-wing applications included no recast layer and no metal splatter from the laser-cutting process.

EXAMPLE 1

Laser Cutting Trials

A Double-Nanosecond-Pulse Laser process using a flexible fiber-hosting laser boroscope system was used to cut a high pressure compressor (HPC) Ti 679 blades and HPC Inco 718 blades representative of potential on-wing care/repair applications. This embodiment used a prototype Nd:YAG laser system with Double-Nanosecond-Pulse settings. The laser cutting rates for the HPC blades were in a range of 0.2 mm/minute to 1.0 mm/minute depending on the thickness and material.

Figure 3:
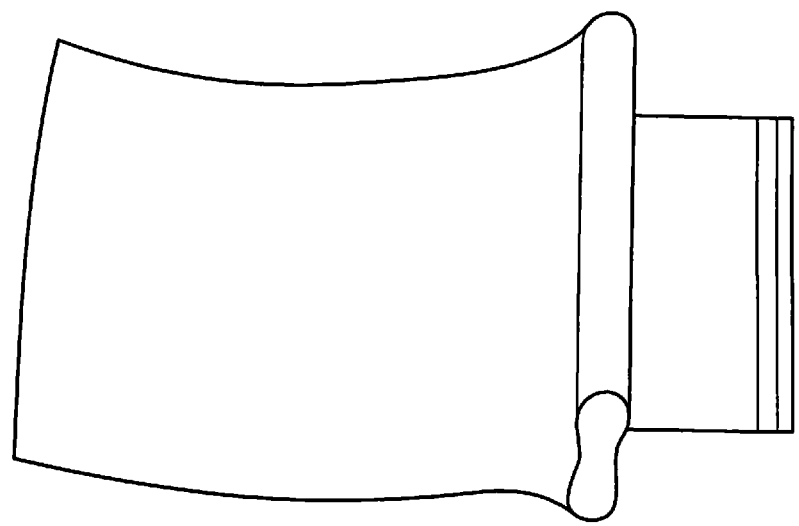
FIG. 3 is a photograph of an Inco 718 blade.
Figure 4:
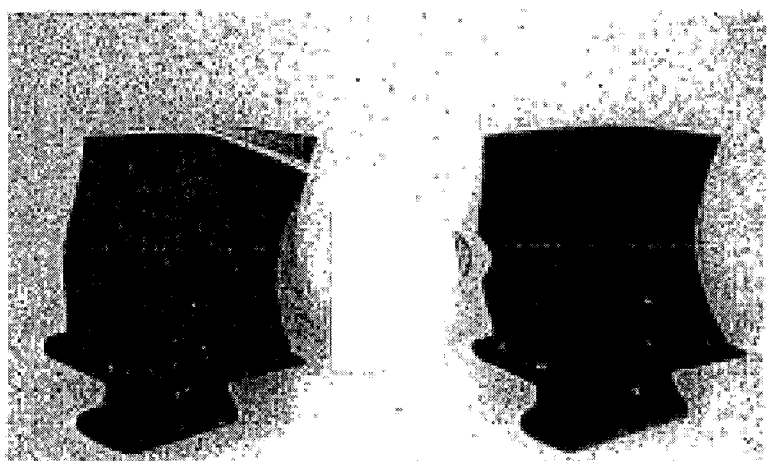
FIG. 4 is a photograph of an Inco 718 blade after a straight cut on the trailing edge of the blade tip made from an embodiment of the present application and an Inco 718 blade after a scalloped cut on the leading edge of the blade made from an embodiment of the present application.
Figure 5:
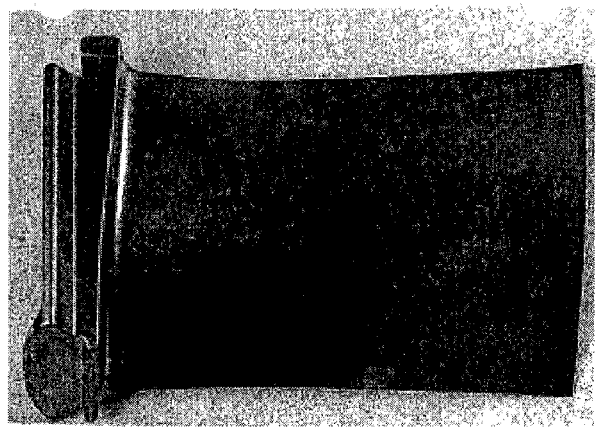

FIGS. 3 and 4 show one of the engine-run HPC Inco 718 blades. FIG. 3 depicts an uncut blade, and FIG. 4 depicts examples of blade cuts. Two (2) HPC Inco 718 blades were used for laser cutting trials. One sample was cut using an embodiment of the double pulse laser system and method of the present application at the blade tip and the other sample was cut at the blade leading edge (L/E), shown in FIG. 3. An arc (8.0 mm chord×5 mm radius) profile piece at the blade L/E was removed with a cutting speed of 1.0 mm/minute. Less than 8 minutes were required to cut the arc profile piece at the blade L/E. The cutting speed at the blade tip was 0.5 mm/minute and approximately 17 minutes were required to cut a 17-mm long straight line at the blade tip.

Figure 5:
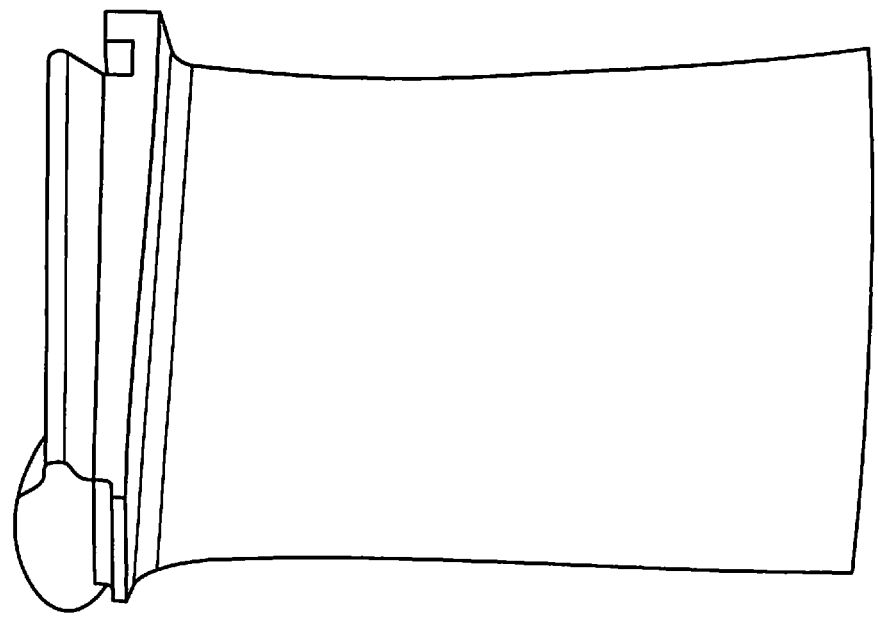
FIG. 5 is a photograph of a Ti 679 blade.
Figure 6:
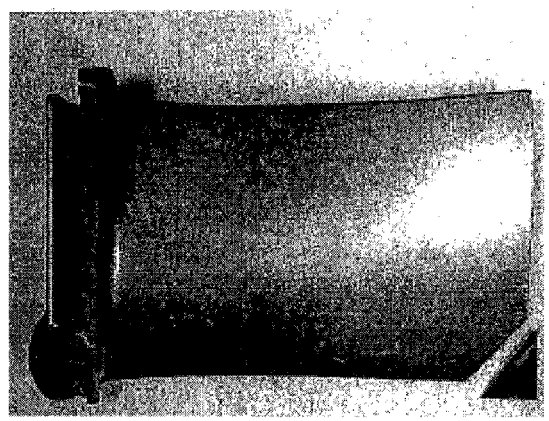
FIG. 6 is a photograph of a Ti 679 blade after a straight cut on the leading edge of the blade tip made from an embodiment of the present application.
Figure 7:
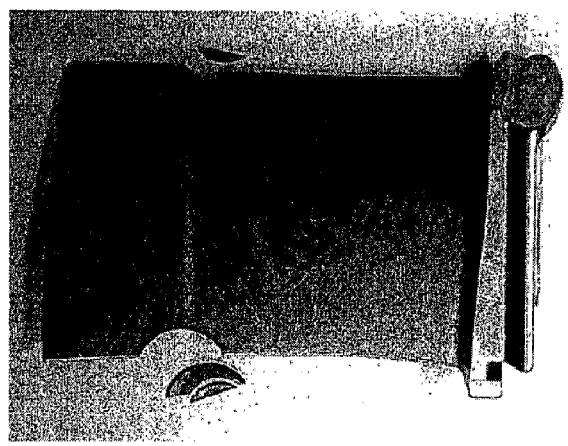
FIG. 7 is a photograph of a Ti 679 blade after a scalloped cut on the trailing edge of the blade and a scalloped cut on the leading edge of the blade made from an embodiment of the present application.

FIGS. 5, 6, and 7 show one of the engine-run HPC Ti 679 blades. FIG. 5 depicts an uncut blade and FIGS. 6 and 7 depict examples of blade cuts. Two (2) blades were used for the laser cutting trials. One blade was laser cut by the double pulse laser system and method at the blade tip with a cutting speed of 0.2 mm/minute due to the increased thickness (2.5 mm) at the blade tip, shown in FIG. 6. Approximately 70 minutes were required to cut a 14-mm long straight line at the blade tip. FIG. 7 shows the Ti blade after laser cutting at the blade L/E and trailing edge (T/E). The cutting speed was 0.5 mm/minute. Approximately 10 minutes were required to remove a small piece at the T/E and about 25 minutes were required to complete the large piece cutting at the L/E both with an arc profile.

During the laser cutting process, material is heated to temperatures far beyond the boiling point, therefore metal droplet transfer was very limited and no re-depositions or splatters were produced. Some discoloration was observed on the laser cut edges of both the Inco 718 and the Ti 679 blade.

Metallographic Evaluation of Recast Layer

Figure 8:
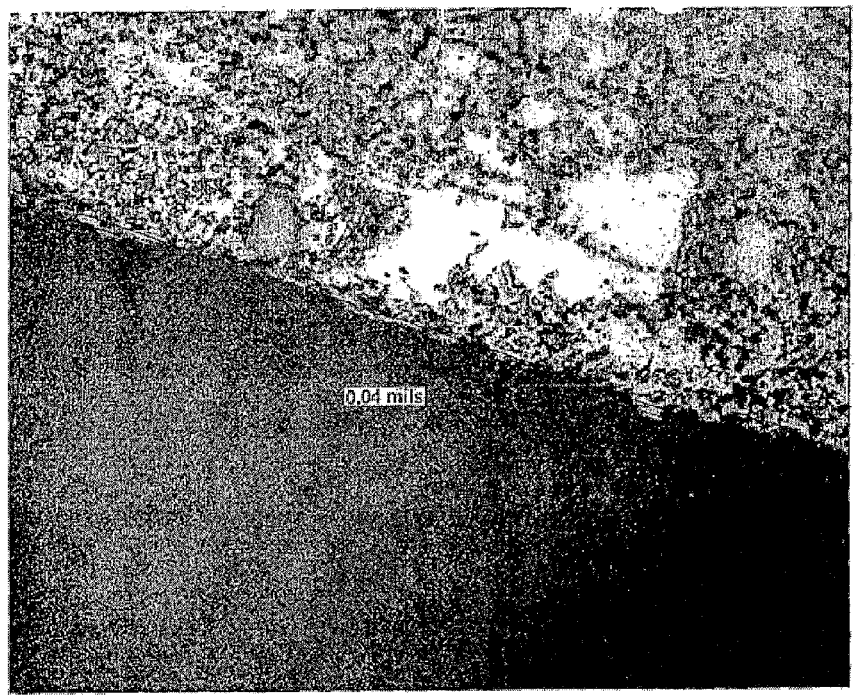
FIG. 8 is a photograph of an Inco 718 blade showing 1.0 μm isolated recast spots.
Figure 9:
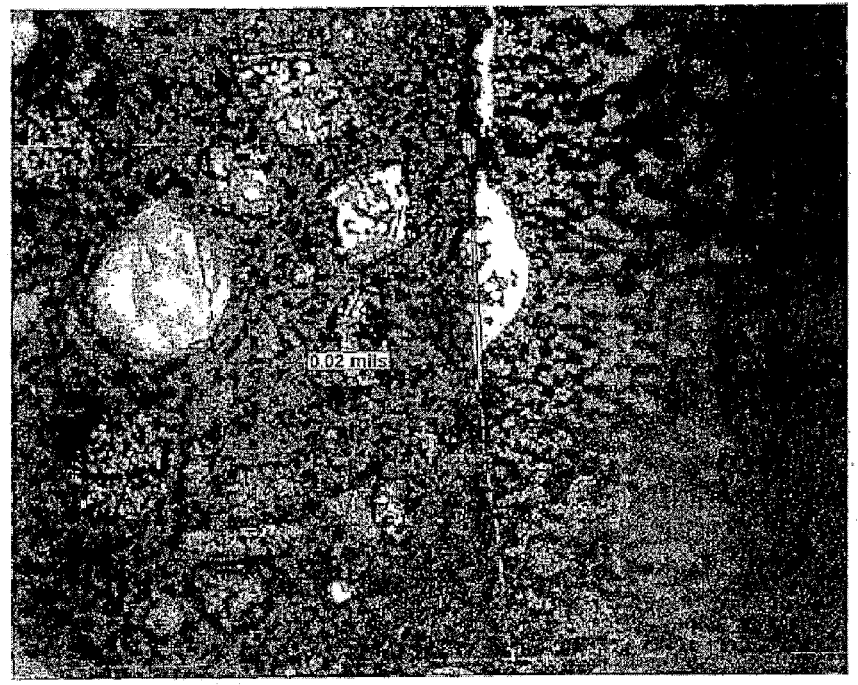
FIG. 9 is a photograph of a Ti 679 blade showing 0.5 μm isolated recast spots.

Metallographic evaluation of the cut edges for the previously presented sample was performed. Results indicated that no continuous recast layers exist at the laser cut edges of both the Inco 718 and Ti 679 blades. There may be some isolated recast spots with a dimension of about 0.5 µm (0.02 mil) for the Ti 679 blades and about 1.0 µm (0.04 mil) for the Inco 718 blades, respectively, shown in FIGS. 8 and 9. FIG. 8 shows metallographic images of the cross-section of Inco 718 blade tip after laser cut. No continuous recast layer was found. The maximum isolated recast spots were about 1.0 µm (0.04 mil) thick. FIG. 9 shows metallographic images of the cross-section of HPC Ti 679 blade tip after laser cut. No continuous recast layer was found. The maximum isolated recast spots were about 0.5 µm (0.02 mil) thick.

Figure 10:
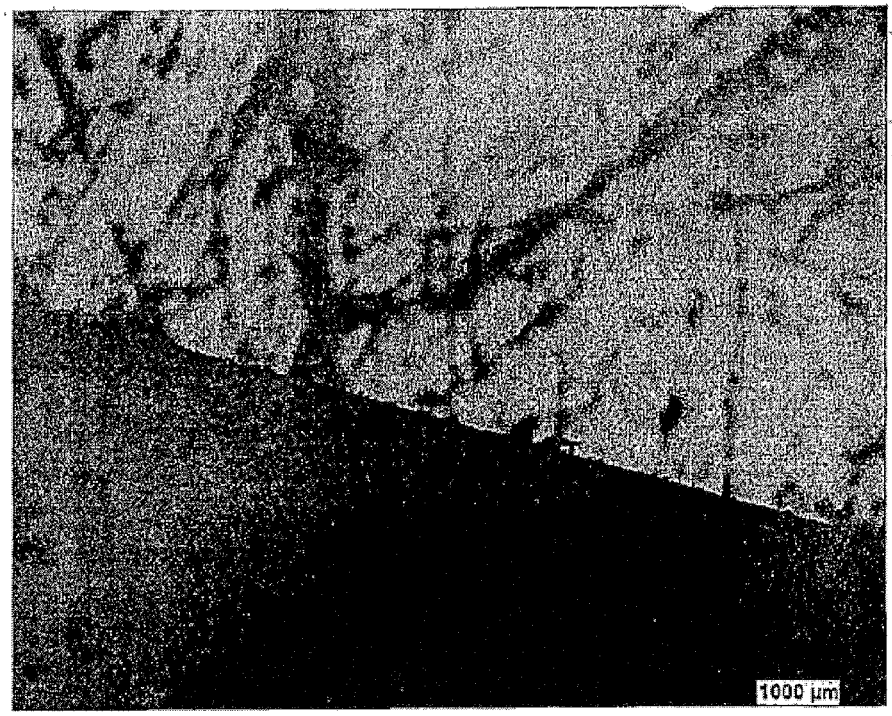
FIG. 10 is a photograph of an Inco 718 blade showing a laser cut edge.
Figure 11:
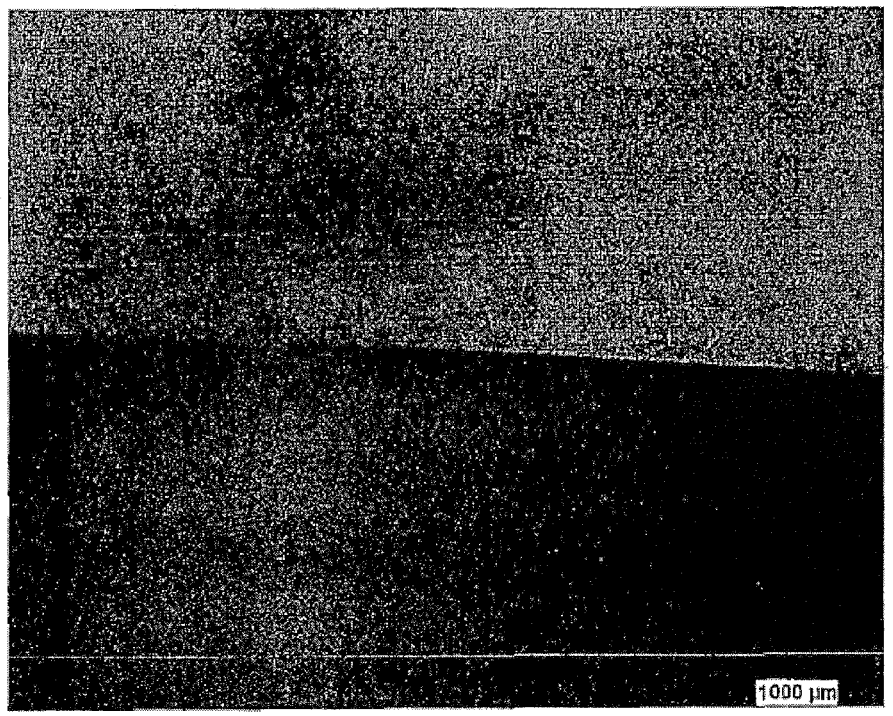
FIG. 11 is a photograph of a Ti 679 blade showing a laser cut edge.

The recast layer for the dual-pulse laser technique is significantly less than the one resulting from conventional laser cutting processes. FIGS. 10 and 11 illustrate acceptable surface finishes of the laser cut edges for each material. It is believed that no post-laser-cutting surface cleaning process (either mechanical or chemical method) would be needed to remove detrimental recast on the cutting surfaces of the blades after the double pulse laser cutting process. The maximum isolated recast spots were about 0.5 µm (0.02 mil) thick for the Ti679 blade in FIG. 10 and 1.0 µm (0.04 mil) thick for the Inco 718 blade in FIG. 11.

One aspect of the present application is an apparatus including a borescope inspection device having a flexible tube that includes an inspection end sized to be inserted through a borescope inspection port of a gas turbine engine which may be positioned on a structure of an aircraft and a coherent electromagnetic energy device including a double pulse laser operable to emit a pair of limited duration laser pulses and possibly at least one fully flexible fiber-hosted laser. The coherent electromagnetic energy device is coupled with the borescope inspection device and is operable to be inserted through the borescope inspection port in proximity with the flexible tube of the borescope inspection device.

A further feature includes the double pulse laser operable to emit a pair of limited duration laser pulses being further capable of affecting a repair at a repair location on the gas turbine engine. The double pulse laser can be operated with an inter-pulse interval time between a first pulse and a second pulse greater than a pulse duration of either the first pulse or the second pulse. In operation the laser can produce a quantity of debris from the repair location of the gas turbine engine which is then superheated to reduce and/or eliminate a recast layer in the repair location of the gas turbine engine. This can also include providing no continuous recast layer and providing a surface finish that meets a surface finish threshold on the repair location of the gas turbine engine.

The inter-pulse interval time may be within a range of 30 ns and 150 ns and an inter-pair interval time is in a range between 100 µs and 100 ms. A process device may also be included which is capable of aiding the coherent electromagnetic energy device to affect a repair at a repair location on the gas turbine engine where the coherent electromagnetic energy device and the process device are coupled with the borescope inspection device and operable to be inserted through the borescope inspection port in proximity with the flexible tube of the borescope inspection device. The coherent electromagnetic energy device may include a laser delivery fiber with a 1.0 mm diameter providing an average output power up to 8 kilowatts.

Another embodiment of the present application is an apparatus including a borescope inspection device having a flexible tube that includes an inspection end sized to be inserted through a borescope inspection port of a gas turbine engine which may be positioned on a structure of an aircraft and a coherent electromagnetic energy device including a double pulse laser which may include at least one fully flexible fiber-hosted laser with a 1.0 mm diameter providing an average output power up to 8 kilowatts. The coherent electromagnetic energy device is coupled with the borescope inspection device and is operable to insert the flexible tube of the borescope inspection device through the inspection port of the gas turbine engine. The borescope inspection device can image a repair location of a gas turbine engine component and the coherent electromagnetic energy device can emit a pair of limited duration laser pulses to affect a repair at the repair location. The double pulse laser system can include an interval time between a first pulse and a second pulse greater than a duration time of either the first pulse or the second pulse and can produce a quantity of debris from the repair location of the gas turbine engine component. The debris can be superheated to eliminate a recast layer in the gas turbine engine component.

Yet another embodiment is for a method including inserting a flexible tube of a borescope inspection device through an inspection port of a gas turbine engine, the flexible tube having an end compatible with a coherent electromagnetic energy device including a double pulse laser; imaging a repair location of a gas turbine engine component with the borescope inspection device; emitting a pair of limited duration laser pulses from the coherent electromagnetic energy device to affect a repair at the repair location, the double pulse laser having an interval time between a first pulse and a second pulse greater than a pulse duration of either the first pulse or the second pulse; producing a quantity of debris from the repair location of the gas turbine engine component; and superheating the quantity of debris to eliminate a recast layer in the gas turbine engine component. The inspection port can further include an opening for a first engine stage and inserting the flexible tube further includes accessing a second engine stage through the inspection port of the first stage. Elimination of the recast layer may further include providing the formation of no continuous recast layer and providing a surface finish on the repair location of the gas turbine engine. The emission of the pair of limited duration laser pulses may be performed in air or with an air flush.

In another aspect the present application provides an apparatus for emitting electromagnetic energy via an emitting end for repairing a component, the apparatus comprising an inspection device having a flexible extension that includes an inspection end sized to be inserted through an inspection opening of an assembly to be repaired, and a coherent electromagnetic energy device including a double pulse laser configured to emit successive pairings of limited duration laser pulses, the coherent electromagnetic energy device coupled with the flexible extension of the inspection device and operable to be inserted through the inspection port of the assembly.

In still a further aspect the present application provides an apparatus comprising a gas turbine engine construction device having a flexible borescope capable of capturing an image of a component to be operated upon and a laser positioned proximate an end of the flexible borescope to emit successive pairings of laser energy pulses, a first pulse of a pairing operable to produce an ejecta from the component and a second pulse of the pairing operable to disperse the ejecta to improve material processing properties.

In yet still a further aspect the present application provides an apparatus comprising an inspection and repair device having a flexible portion configured to convey a borescope and a laser, the laser including means to discourage a recast layer when a laser energy is irradiated upon a repair component.

In still another aspect the present application provides a method comprising inserting a flexible portion of a borescope inspection device through an inspection port of a gas turbine engine, the flexible portion having an end coupled with a coherent electromagnetic energy device including a double pulse laser, emitting a pair of limited duration laser pulses from the coherent electromagnetic energy device to affect a change in physical state of a portion of the gas turbine engine, producing a quantity of debris from a location of the gas turbine engine component as a result of a first pulse of the double pulse laser irradiating the gas turbine engine, and heating the quantity of debris with a second pulse of the double pulse laser.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus for emitting electromagnetic energy comprising
    an inspection device having a flexible extension that includes an
    inspection end sized to be inserted through an inspection opening of an assembly to be repaired; and
    a coherent electromagnetic energy device including a pulse laser operable to emit laser pulses at a discharge, the coherent electromagnetic energy device coupled with the flexible extension of the inspection device and operable to be inserted through the inspection opening of the assembly,
    wherein the pulse laser is a double pulse laser configured to emit successive pairings of limited duration laser pulses including a primary and a secondary laser pulse that are each about 3 ns in duration with an average intensity of about 4 Mega Watts per square centimeter producing a maximum power of about 750 kw, and wherein the interpulse time between pairs is between about 30 ns and about 150 ns.

2. The apparatus of claim 1, wherein the inspection device includes a borescope coupled to the flexible extension, the borescope operable to provide an inspection image.

3. The apparatus of claim 1, which further includes an assembly space having positioned within it a gas turbine engine that includes a damaged component, the inspection opening formed within a portion of the gas turbine engine.

4. The apparatus of claim 1, wherein the time between a first pair of limited duration laser pulses and a second pair of limited duration laser pulses is greater than a time between the pulses of either the first pair or second pair.

5. An apparatus comprising
    a gas turbine engine construction device having a flexible borescope capable of capturing an image of a component to be operated upon and a laser positioned proximate an end of the flexible borescope to emit successive pairings of laser energy pulses, a first pulse of a pairing operable to produce an ejecta from the component and a second pulse of the pairing operable to disperse the ejecta to improve material processing properties wherein the first pulse and the second pulse of the successive pairings are each about 3 ns in duration with an average intensity of about 4 Mega Watts per square centimeter producing a maximum power of about 750 kw, and wherein an interpulse time between the successive pairings is between about 30 ns and about 150 ns.

6. The apparatus of claim 5, which further includes a gas turbine engine that has an opening sized to receive the flexible borescope; wherein the gas turbine engine includes the component to be operated upon; and further wherein the component is metallic.

7. The apparatus of claim 5, wherein the flexible borescope includes a cross sectional dimension less than about 1 cm along a length of the flexible borescope.

8. The apparatus of claim 5, wherein the laser is a fiber-hosted laser and is capable of providing an average output power of above 1 kW and a peak power of more than 50 kW.

9. The apparatus of claim 5, wherein the second pulse of the pairing vaporizes the recast layer.

10. The apparatus of claim 5, wherein the second pulse of the pairing discourages formation of a recast layer of the component.

11. A method comprising inserting a flexible portion of a borescope inspection device through an inspection port of a gas turbine engine, the flexible portion having an end coupled with a coherent electromagnetic energy device including a double pulse laser;

emitting a pair of limited duration laser pulses from the coherent electromagnetic energy device to affect a change in physical state of a portion of the gas turbine engine;

producing a quantity of debris from the portion of the gas turbine engine as a result of a first pulse of the double pulse laser irradiating the gas turbine engine; and heating the quantity of debris with a second pulse of the double pulse laser, wherein the first pulse and the second pulse of the double pulse laser pulses are each about 3 ns in duration with an average intensity of about 4 Mega Watts per square centimeter producing a maximum power of about 750 kw, and wherein an interpulse time between the successive pairings is between about 30 ns and about 150 ns.

12. The method of claim 11, which further includes flushing the repair location of the gas turbine engine with a working fluid.

13. The method of claim 11, wherein the heating includes superheating the quantity of debris.

14. The method of claim 11, wherein the heating further includes discouraging a recast layer in the gas turbine engine.

15. The method of claim 11, wherein the irradiating includes emitting a laser pulse for about 3 ns.

16. The method of claim 11, wherein the location is a repair location and which further includes imaging the repair location with the borescope inspection device.

17. The method of claim 16, wherein the producing includes removing a damaged portion of a gas turbine engine airfoil.

18. The method of claim 11, which further includes dwelling for a time between the first pulse and the second pulse longer than a duration of the first pulse or the second pulse.

19. The method of claim 18, which further includes emitting another pair of limited duration laser pulses after the pair of limited duration laser pulses, the time between the another pair and the pair being longer than the dwelling.

20. The method of claim 19, wherein the emitting another pair of limited duration laser pulses after the pair of limited duration laser pulses is between 100 µs and 100 ms.

21. The method of claim 11, which further includes performing one of a removing material from the portion of the gas turbine engine, building up a material on the portion of the gas turbine engine, joining a component to the portion of the gas turbine engine, and treating the portion of the gas turbine engine.

22. The method of claim 21, wherein the removing includes one of cutting and hole drilling.

23. The method of claim 21, wherein the building includes adding metal.

24. The method of claim 21, wherein the joining includes one of brazing, welding, and bonding.

25. The method of claim 21, wherein the treating includes one of heat treating, peening, re-surfacing, and surface cleaning.

26. An inspection and repair apparatus comprising an elongate member capable of being flexibly routed within a workpiece and having an imager located near an insertion end of the member capable of capturing electromagnetic energy from within a workpiece;

a feed stock conveyor coupled with the elongate member and operable to deliver a feed stock to a work area of the workpiece, the work area having a preworked shape and a desired post-work shape;

a laser disposed near the insertion end of the elongate member and capable of lasing the workpiece;

wherein the laser interacts with the feed stock in the repair area and both laser and feed stock are manipulated using information from the imager to produce a near net shape repaired component of the workpiece wherein the laser is configured to emit successive pairings including a first pulse and a second pulse each about 3 ns in duration with an average intensity of about 4 Mega Watts per square centimeter producing a maximum power of about 750 kw, and wherein the laser is configured to provide an interpulse time between the successive pairings of between about 30 ns and about 150 ns.

27. The method of claim 26, wherein the feed stock is one of a powder, a gas, and a wire.

28. The method of claim 26, wherein the workpiece is a gas turbine engine and the component is an airfoil member of the gas turbine engine.

29. An inspection and repair apparatus comprising a portable imaging and repair system capable of being transported between locations in which an imaging and repair operation is performed, the system including a flexible elongate borescope having an imager capable of capturing electromagnetic emissions from a component to be operated upon and a display in communication with the imager capable of providing information of the electromagnetic emissions to an operator, the system also including a laser capable of changing the state of a material associated with the component;

wherein the laser, display, and imager can be placed in an arrangement that permits the portable imaging and repair system to be readily moved from a first location to a second location; and the laser is configured to emit successive pairings including a first pulse and a second pulse each about 3 ns in duration, with an interpulse time between the successive pairings of between about 30 ns and about 150 ns, and the laser is configured to move at a speed rate between about 0.2 millimeters per minute and about 1.0 millimeters per minute.

30. The method of claim 29, wherein the arrangement includes having at least one of the laser, display, and imager de-coupled from the portable imaging and repair system.

31. The method of claim 29, wherein the laser is capable of emitting an energy sufficient to remove material from the component.

32. A method comprising
inserting a flexible portion of a borescope inspection device and a laser positioned on a proximate end of the borescope through an inspection port of a gas turbine engine,
directing the laser toward an apparatus to be repaired, and
cutting the apparatus with the laser by (i) emitting a first pulse and a second pulse from the laser, wherein the first pulse and the second pulse each have an average intensity of about 4 Mega Watts per square centimeter producing a maximum power of about 750 kw, and (ii) moving the laser along the apparatus at an average rate of between about 0.2 mm/min and 1.0 mm/min wherein the first pulse has a pulse duration of about 3 nanoseconds and the second pulse has a duration of about 3 nanoseconds; and wherein a time between the first pulse and the second pulse is between about 30 nanoseconds and about 150 nanoseconds.

33. The method of claim 32, wherein the apparatus comprises an Inconel, titanium, or nickel alloy.

* * * * *